United States Patent
Shu et al.

(10) Patent No.: US 11,045,106 B2
(45) Date of Patent: Jun. 29, 2021

(54) SYSTEM AND METHOD FOR DETECTING AND DIAGNOSING DISEASES AND USE OF SAME

(71) Applicant: ThermovisionUSA, Inc., Torrance, CA (US)

(72) Inventors: Julius Chin-Hong Shu, Torrance, CA (US); Robert C. Allison, Torrance, CA (US)

(73) Assignee: THERMOVISIONUSA, INC., Torrance, CA (US)

( * ) Notice: Subject to any disclaimer, the term of this patent is extended or adjusted under 35 U.S.C. 154(b) by 0 days.

(21) Appl. No.: 16/761,200

(22) PCT Filed: Oct. 22, 2019

(86) PCT No.: PCT/US2019/057445
§ 371 (c)(1),
(2) Date: May 1, 2020

(87) PCT Pub. No.: WO2020/086586
PCT Pub. Date: Apr. 30, 2020

(65) Prior Publication Data
US 2020/0289020 A1    Sep. 17, 2020

Related U.S. Application Data

(60) Provisional application No. 62/748,927, filed on Oct. 22, 2018.

(51) Int. Cl.
*A61B 5/0507* (2021.01)
*A61B 5/00* (2006.01)

(52) U.S. Cl.
CPC .......... *A61B 5/0507* (2013.01); *A61B 5/0022* (2013.01); *A61B 5/6804* (2013.01);
(Continued)

(58) Field of Classification Search
CPC ... A61B 5/0507; A61B 5/0022; A61B 5/6804; A61B 2560/0214; A61B 2562/0271; A61B 2562/166
See application file for complete search history.

(56) References Cited

U.S. PATENT DOCUMENTS 6,330,479 B1     12/2001   Stauffer
2013/0225988 A1*  8/2013   Mahfouz ................ A61B 5/708
                                                    600/430
(Continued)

OTHER PUBLICATIONS

PCT/US/2019/57445; International Search Report and Written Opinion dated Jan. 14, 2020. 17 pages.

*Primary Examiner* — Kaylee R Wilson
*Assistant Examiner* — Jay B Shah
(74) *Attorney, Agent, or Firm* — Cislo & Thomas, LLP; Katherine B. Sales

(57) ABSTRACT

A system and method for detecting disease comprising a device for detecting angiogenesis and an electronic device. The device comprises two microwave scanners, at least one multiple channel radiometer, a microwave switch network, a controller, a data transmission device, and a power source. Each microwave scanner comprises a cup; a flexible printed circuit board, each circuit board comprising: a plurality of antenna modules coupled thereto, each antenna module comprising: an antenna, a multi-throw microwave switch, and a temperature sensor. The antenna is configured to receive microwaves thermal radiation from patient tissue and the radiometer is configured to measure microwaves thermal radiation emitted from patient tissue. The data transmission device is configured to wirelessly transmit measurement data collected by the controller from the radiometer and the temperature sensors to an electronic device and the electronic device is configured to transmit the measurement data to a cloud data storage.

17 Claims, 11 Drawing Sheets

(52) U.S. Cl.
CPC ........... *A61B 2560/0214* (2013.01); *A61B 2562/0271* (2013.01); *A61B 2562/166* (2013.01)

(56) References Cited

U.S. PATENT DOCUMENTS

| | | | |
|---|---|---|---|
| 2014/0276031 A1* | 9/2014 | Lomnitz | A61B 5/4312 |
| | | | 600/430 |
| 2015/0182121 A1 | 7/2015 | Barbour et al. | |
| 2016/0051221 A1 | 2/2016 | Dickhans et al. | |
| 2018/0058945 A1* | 3/2018 | Vesnin | G01K 13/002 |
| 2018/0249767 A1* | 9/2018 | Begriche | A61B 5/0492 |

* cited by examiner

SYSTEM AND METHOD FOR DETECTING AND DIAGNOSING DISEASES AND USE OF SAME

CROSS-REFERENCE TO RELATED APPLICATION

This application claims priority to and is a national phase entry of International Application No. PCT/US 19/57445, entitled "System and Method for Detecting and Diagnosing Diseases and Use of Same," filed Oct. 22, 2019, which claims the benefit of U.S. Provisional Application No. 62/748,927, entitled "AIM Eco-system of Cyber Tele-Healthcare for Breast Wellness and Disease Screening," filed Oct. 22, 2018, which applications are incorporated in their entirety herein by this reference.

BACKGROUND OF THE INVENTION

After a cell mutates into a cancer cell, the human body triggers the process of angiogenesis, where the human body will naturally raise the temperature of the cancer cell to a degree that is higher than the surrounding healthy cells in an effort to provide nutrition for the high metabolism activity of cancer cells. Angiogenesis is not limited to cancer and is a process that the human body undergoes in response to many different diseases. This increase in cell temperature is called a thermal biomarker. Properly designed microwave scanners containing an antenna, a radiometer and related electronic devices can spot and detect the thermal biomarkers, however, they are unable to differentiate between the human body's response to different diseases, namely the "heat source" that causes the existence of the detected thermal biomarker.

As such, there is a need for an improved system and method for detecting and diagnosing diseases.

The present invention overcomes several of the deficiencies, disadvantages and undesired parameters associated with known systems and methods for detecting and diagnosing diseases.

SUMMARY OF THE INVENTION

According to one embodiment of the present invention, there is provided a system for detecting disease, the system comprising a device for detecting angiogenesis and an electronic device comprising a smart phone, tablet, or computer.

The device for detecting angiogenesis comprises two microwave scanners, at least one multiple channel radiometer, at least one microwave switch network, at least one controller electrically coupled to both microwave scanners, at least one data transmission device electrically coupled to the controller, and at least one power source.

Each microwave scanner comprises a cup, a flexible printed circuit board coupled to the cup, each circuit board comprising a plurality of antenna modules coupled thereto, each antenna module comprising an antenna configured to receive microwaves from patient tissue; at least one multi-throw microwave switch coupled to the antenna; and at least one temperature sensor located in close proximity to each antenna configured to take temperature measurements.

The radiometer is coupled to the plurality of antenna modules by coaxial cable and is configured to measure microwaves emitted from a patient's internal tissue.

The microwave switch network is coupled to the multi-throw microwave switch and is configured to perform a switching sequence.

The controller is configured to command both the microwave switch switching sequence and the sequence of the temperature sensor measurements; and collect measurement data from the radiometer and the temperature sensors.

The data transmission device is configured to wirelessly transmit the measurement data collected by the controller from the radiometer and the temperature sensors to the electronic device.

The power source comprises at least one rechargeable battery.

The electronic device is configured to receive the measurement data from the data transmission device and transmit the measurement data to a cloud data storage.

Optionally, the system can further comprise a cloud data storage configured to the measurement data from the electronic device.

In another embodiment, the present invention comprises a device for detecting angiogenesis, the device comprising: two microwave scanners, each microwave scanner comprising: a flexible printed circuit board comprising: a plurality of antenna modules coupled thereto, each antenna module comprising: an antenna configured to receive microwaves from patient internal tissue; at least one multi-throw microwave switch coupled to the antenna; and at least one temperature sensor located in close proximity to each antenna configured to take temperature measurements; at least one multiple channel radiometer coupled to the plurality of antenna modules by coaxial cable configured to measure microwaves emitted from patient tissue; at least one microwave switching network coupled to the multi-throw microwave switch and the radiometer configured to perform a switching sequence; and at least one controller electrically coupled to both microwave scanners and configured to: command both the microwave switch switching sequence and the sequence of the temperature sensor measurements; and collect measurement data from the radiometer and the temperature sensors; at least one data transmission device electrically coupled to the controller and configured to wirelessly transmit the measurement data collected by the controller from the radiometer and the temperature sensors to an electronic device; and at least one power source comprising at least one rechargeable battery.

Optionally, the microwave scanner further comprises at least one cup and the at least one flexible printed circuit board is coupled to the at least one cup.

Optionally, the device is a garment with two cups and the microwave scanners are coupled to the cups.

Optionally, the garment cups comprise at least one layer of electrically conductive cloth.

Optionally, the garment is in the form of a bra.

In another embodiment, the present invention is directed to a device for detecting angiogenesis, the device comprising: at least one microwave scanner, the microwave scanner comprising: a flexible printed circuit board comprising: a plurality of antenna modules coupled thereto, each antenna module comprising: an antenna configured to receive microwaves from internal patient tissue; at least one multi-throw microwave switch coupled to the antenna; and at least one temperature sensor located in close proximity to each antenna configured to take temperature measurements; at least one controller electrically coupled to the at least one microwave scanner and configured to: command both the microwave switch switching sequence and the sequence of the temperature sensor measurements; and collect measurement data from the radiometer and the temperature sensors; at least one data transmission device electrically coupled to the controller and configured to wirelessly transmit the measurement data collected by the controller from the radiometer and the temperature sensors to an electronic device; and at least one power source.

Optionally, the power source comprises a power cord.

In another embodiment, the present invention is directed to a method of using the device. The method comprises the steps of:

a) providing the device;
b) placing the device on a user's skin;
c) scanning a user's subcutaneous tissue to produce measurement data from the radiometers and temperature sensors;
d) transmitting the measurement data from the device to an electronic device; and
e) transmitting the measurement data from the electronic device to a cloud data storage.

Optionally, the method can further comprise step f) after step e), processing the measurement data to determine suspicious sites in the patients tissue.

DRAWINGS

These and other features, aspects and advantages of the present invention will become better understood with reference to the following description, appended claims, and accompanying drawings where:

DETAILED DESCRIPTION OF THE INVENTION

The following discussion describes in detail one embodiment of the present invention and several variations of that embodiment. This discussion should not be construed, however, as limiting the invention to those particular embodiments. Practitioners skilled in the art will recognize numerous other embodiments as well.

Definitions

As used herein, the following terms and variations thereof have the meanings given below, unless a different meaning is clearly intended by the contest in which such term is used.

The terms "a," "an," and "the" and similar referents used herein are to be construed to cover both the singular and the plural unless their usage in context indicates otherwise.

As used in this disclosure, the term "comprise" and variations of the term, such as "comprising" and "comprises," are not intended to exclude other additives, components, integers ingredients or steps.

The terms "couple," "coupled," "couples," and "coupling," refer to connecting two or more elements or signals electrically, mechanically, or otherwise. Two or more electrical elements may be electrically coupled, but not mechanically or otherwise coupled; two or more mechanical elements may be mechanically coupled, but not electrically or otherwise coupled; two or more electrical elements may be mechanically coupled, but not electrically or otherwise coupled. Coupling (whether mechanical, electrical, or otherwise) may be for any length of time, e.g., permanent, semi-permanent, or only for an instant.

The Invention

The system 100 as discussed in this application is with respect to detecting and diagnosing breast cancer, but the system 100 is not limited to breast cancer. The system 100 can be adapted to detect and diagnose many different types of diseases and the hardware can be adapted as necessary to accommodate different parts of the human body. Additionally, this system and method is not limited to use on humans. The system and method can also be adapted for use on other subjects, such as animals.

Figure 1:
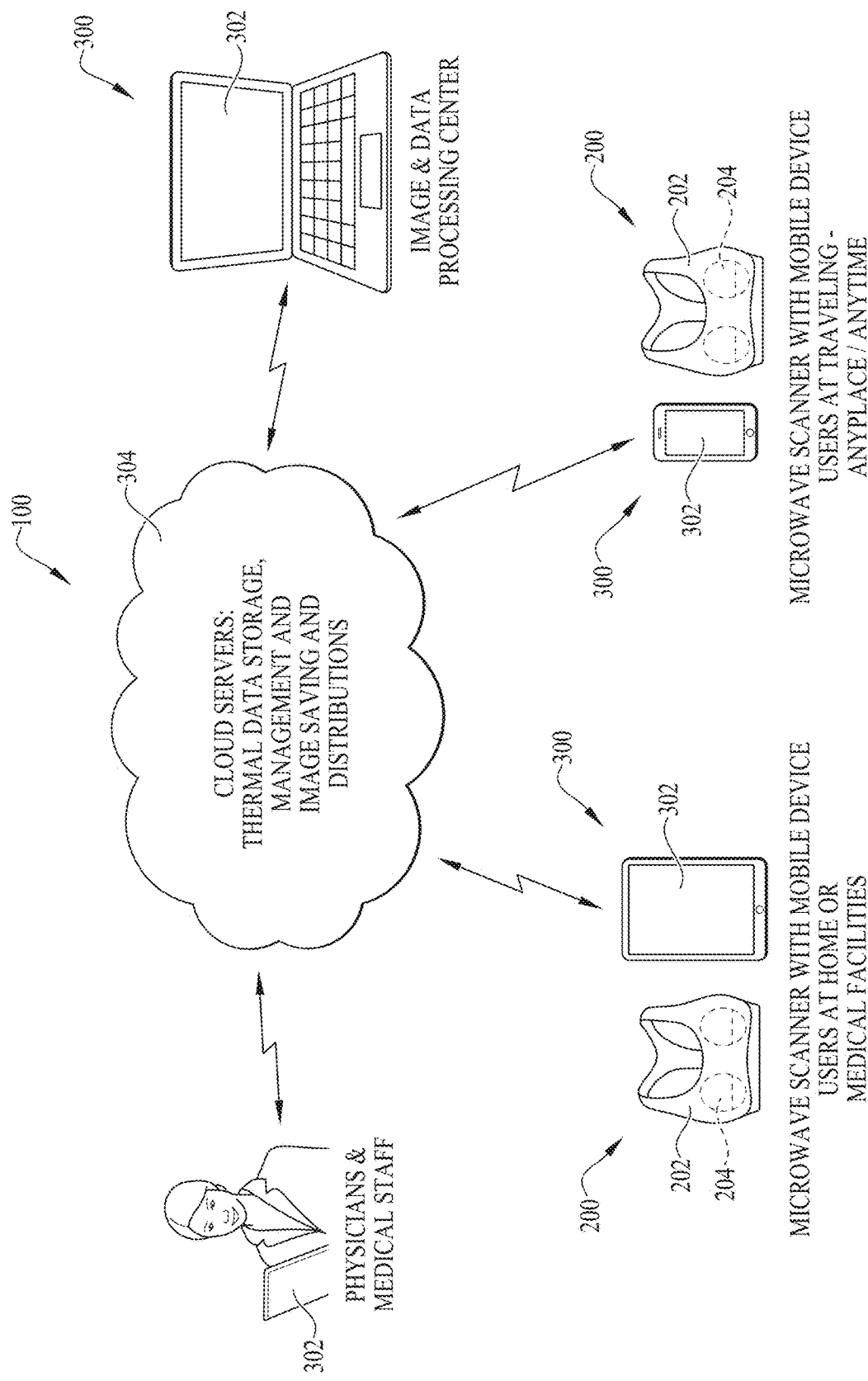
FIG. 1 is a schematic view of a system for detecting and tele-diagnosing diseases having features of the present invention, wherein a device for detecting disease is included therein.

Referring now to FIG. 1, there is shown a system 100 for detecting and diagnosing diseases. The system 100 comprises two main components: hardware 200 and software 300, and the software 300 can comprise an application that can be used in connection with at least one electronic device 302. Several additional programs can also be used to process and analyze the data and image classification produced by use of the system 100. The electronic device 302 may be a mobile device such as a tablet computer, mobile computer or smartphone, but may also be embodied in any one of a wide variety of wired and/or wireless computing devices, including a wired desktop computer. FIG. 1 depicts the use of the device 200 and program and/or application 300 with a smartphone, tablet and laptop computer 302. The electronic device 302 includes a processing device (processor), input/output interfaces, a display, a network interface, a memory, an operating system, and storage. The electronic device 302 may also include a touchscreen user interface for ease of use and a wireless device, such as Bluetooth, communicating across a local data bus. The system 100 also comprises cloud data storage 304.

The processing device may include any custom-made or commercially available processor, a central processing unit (CPU), or an auxiliary processor among several processors associated with the electronic device, a semiconductor based microprocessor (in the form of a microchip), a macroprocessor, one or more application specific integrated circuits (ASICs), a plurality of suitably configured digital logic gates, and other electrical configurations comprising discrete elements both individually and in various combinations to coordinate the overall operation of the system.

The memory can include any one of a combination of volatile memory elements (e.g., random-access memory (RAM, such as DRAM, and SRAM, etc.)) and nonvolatile memory elements. The memory typically comprises native operating system, one or more native applications, emulation systems, or emulated applications for any of a variety of operating systems and/or emulated hardware platforms, emulated operating systems, etc.

The invention may include application specific software 300, which may comprise some or all the components of the electronic devices 302 and the cloud data storage 304. In accordance with such embodiments, the components are stored in memory and executed by the processing device. The system and method for detecting and diagnosing disease may be resident in the memory of the electronic device 303 and/or optionally the cloud data storage 304.

One of ordinary skill in the art will appreciate that the memory can, and typically will, comprise other components that have been omitted for purposes of brevity. In the context of this disclosure, a non-transitory computer-readable medium stores one or more programs for use by or in connection with an instruction execution system, apparatus, or device.

An electronic device network interface may comprise various components used to transmit and/or receive data over a networked environment via wired and/or wireless means. When such components are embodied as an application, the one or more components may be stored on a non-transitory computer-readable medium and executed by the processing device.

Optionally, the system 100 can incorporate the Internet of Medical Things (IofMT). Also known as healthcare Internet of Things, the IofMT comprises the medical devices and applications connected to healthcare IT systems via the internet. Wi-Fi enabled devices facilitate machine-to-machine communication and link to cloud platforms for data storage and management.

Figure 2:
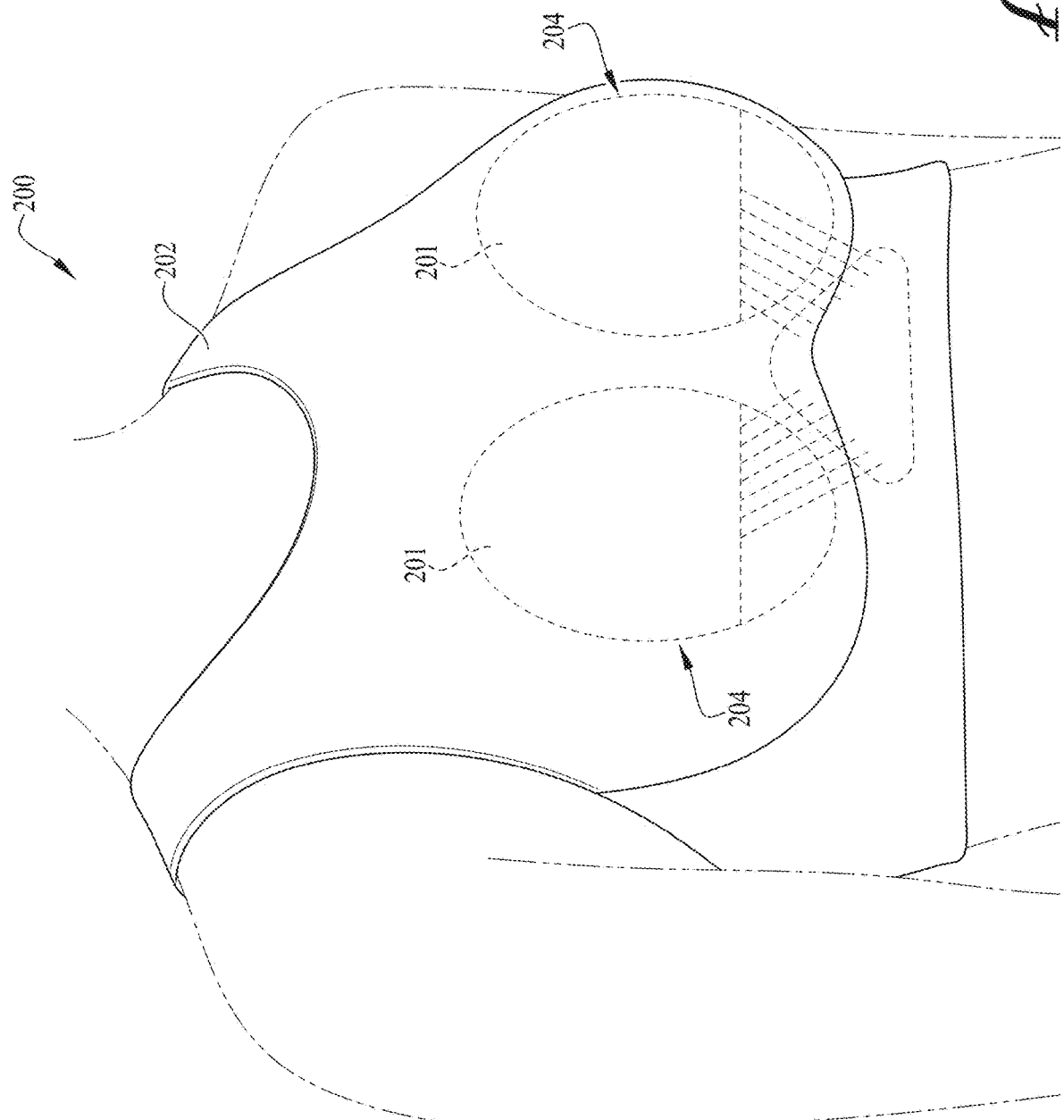
FIG. 2 is a perspective view of the device of FIG. 1, where the device can be seen within a garment.
Figure 3:
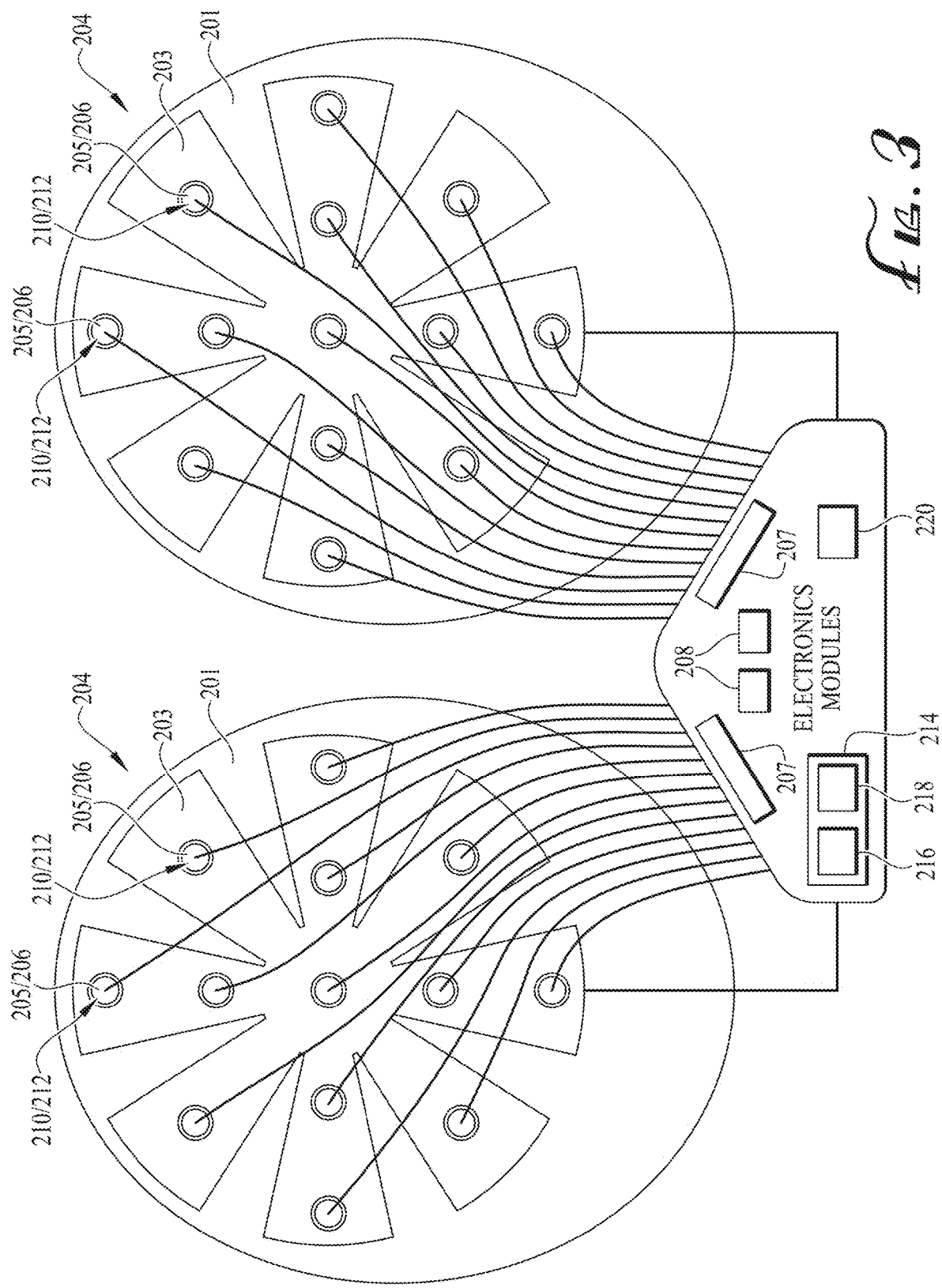
FIG. 3 is an enlarged sectional view of the device of FIG. 2, wherein a back surface of the microwave scanner cups has been removed to show the internal components.
Figure 4:
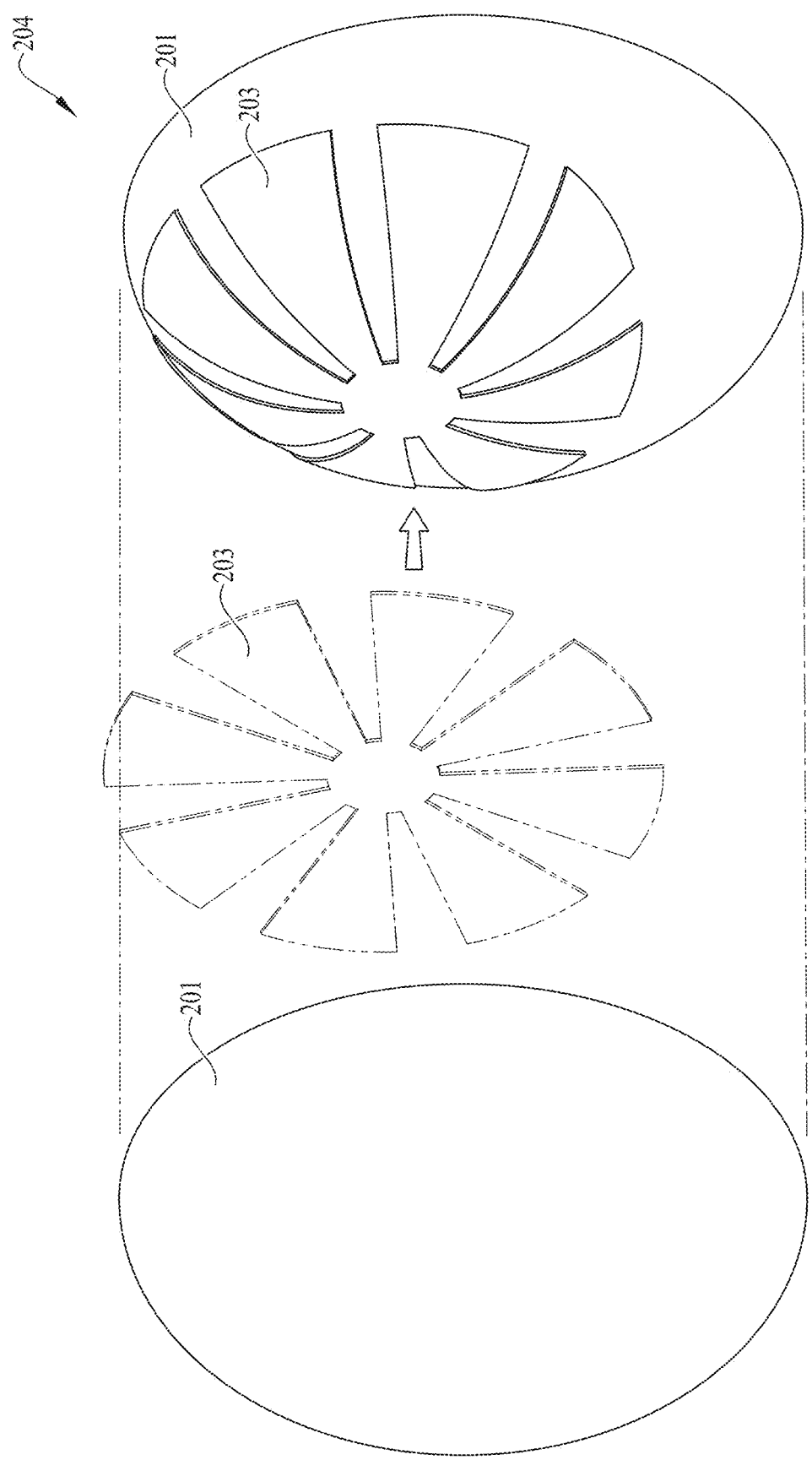
FIG. 4 is an exploded view of the microwave scanner cups of the device, where a flexible circuit board can be seen.

Referring now to FIGS. 2, 3 and 4, the hardware 200 comprises a wearable garment 202 and at least one microwave scanner 204. Each microwave scanner 204 is electrically coupled to electrical components that control the microwave scanners 204. Optionally, as shown in FIGS. 2 and 3, all of the electrical components can be mounted/coupled to a central support. The electrical components mounted to the support comprise the microwave switch network 207, radiometers 208, and an electrical module 214 that comprises at least one controller 216 and at least one data transmission device 218. The battery/power source 220 can also be coupled to the central support.

Optionally, as shown in FIGS. 2, 3, and 4, each microwave scanner 204 can comprise a cup 201 within which, or mounted to, is a flexible printed circuit board (FPCB) 203. Coupled to the flexible printed circuit board 203 are the antenna modules 206. Each antenna module 206 comprises an antenna 205 and a microwave switch 210. Cables connect each antenna 205 to a microwave switch network 207 and/or their radiometer 208. In this application the garment 202 is in the form of bra-like garment, and it can be made to support and connect two microwave scanner cups 201 so that the cups 201 firmly touch the breast skin. An electrically conductive cloth pad can be coupled to the inside the scanner cup 201 to provide shielding from external microwave interference sources. The electrically conductive pad would be placed up against the user's skin when the device 200 is worn. Optionally the cup 201 comprises at least one piece of electrically conductive cloth. Optionally the cup 201 can also comprise thermal insulation to provide thermal insulation from external temperature influences. FIG. 4 is an exploded view of the microwave scanner 204 that shows how the flexible PCB (Printed Circuit Board) 203 can conform to the shape and size of the breast it is being applied to. The cup 201 can either comprise two separable halves, where the flexible PCB 203 is mounted in between the two halves, or the flexible PCB 203 can be embedded within the cup 201. The cup 201 can be made from a rigid material such as plastic, but preferably the cup 201 is made from a semi-flexible material that can conform to the shape of the user's breast it is being applied to.

The microwave scanner ("M-S") 204 can comprise at least three different types of configurations, depending on its application: Type 1: M-S is a Single-Antenna Single-Channel (SASC) microwave radiometer (aka M-R); Type 2: M-S is a Multiple-Antenna-Single-Channel (MASC) M-R; and Type 3: M-S is a Multiple-Antenna-Multiple-Channel (MAMC) M-R. Type 1 is essentially a special subset of either Type 2 or Type 3. Type 3 comprises at least one microwave switching network 207 coupling multiple antenna modules 206 and multiple-channel radiometers 208. These different configurations will be discussed in more detail below. All three configurations have a cable and/or wireless interface located in the electronics module 214 and can connect to an electronic device 302 for data link through the electronic device 302 to the main data storage areas 304. As shown in FIG. 1, the main data storage areas 304 are located at cloud servers that are accessible by Wi-Fi and Internet.

Figure 5:
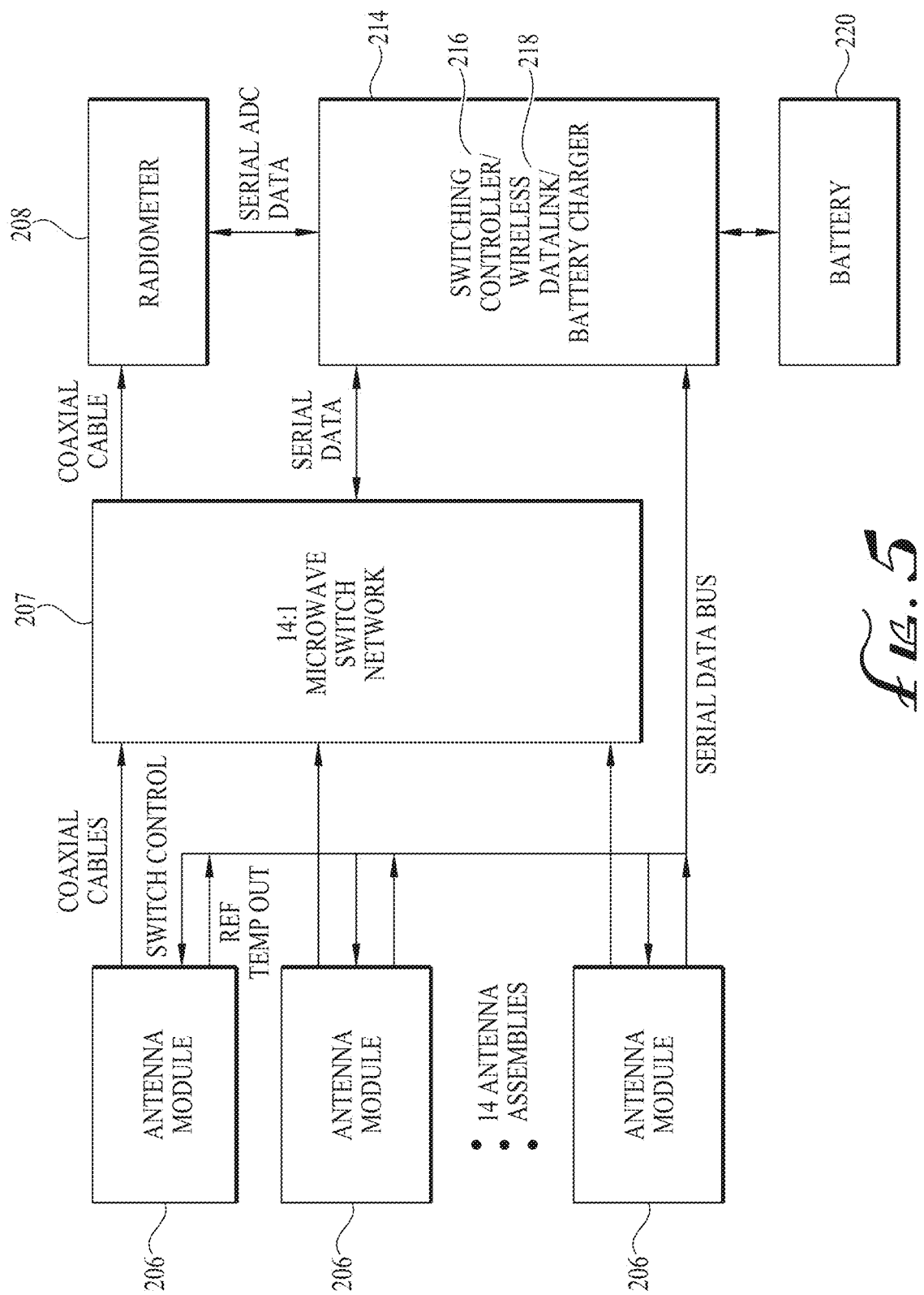
FIG. 5 is a block diagram of the electronic process of the device of FIG. 2.

FIG. 5 shows the block diagram of the microwave scanner 204 that is coupled to the garment 202 to form the type 2 hardware device 200. As noted above, the microwave scanner 204 comprises at least one antenna module 206, each antenna module 206 comprising at least one antenna 205 and at least one microwave switch 210. The antenna modules 206 are coupled to the microwave switch network 207 via coaxial cables. Both the microwave switch network 207 and the radiometers are coupled to the electronics module 214, which is itself coupled to the power source (battery) 220. The electronics module 214 is electrically coupled to the microwave scanner 204 through the serial data link and as noted above comprises at least one controller 216 and at least one data transmission device 218.

The antenna modules 206 receive and capture the naturally occurring microwave thermal transmissions from the internal tissue of the human body. The microwave scanner 204 also comprises at least one radiometer 208, and preferably comprises a plurality of multiple channel radiometers 208 to concurrently collect a larger amount of thermal data to facilitate the thermal profile and signature determination. The radiometers 208 convert the microwave thermal energy intensity (aka thermal brightness) emitted from the tissue that is captured by the antennas 206 into electrical energy in terms of voltages and currents and then calibrate this electrical energy to the temperature (thermal energy). Typically the microwaves are emitted at millimetre-to-centimetre wavelengths, corresponding to frequencies of 1-100 GHz range. The emissivity of thermal radiation through specific body tissues depends on the frequency (or wavelength). The proper selection of the frequency band inside the microwave spectrum is crucial for the device 200 to achieve its anticipated accuracy and sensitivity. The antennas 206 are coupled to their respective radiometers 208 by coaxial cable or optionally by a waveguide. A waveguide is a structure that guides waves, such as electromagnetic waves or sound waves, with minimal loss of energy by restricting expansion to one dimension or two. There is a similar effect in water waves constrained within a canal, or guns that have barrels which restrict hot gas expansion to maximize energy transfer to their bullets. Without the physical constraint of a waveguide, wave amplitudes decrease according to the inverse square law as they expand into three-dimensional space. There are different types of waveguides for each type of microwave. The original and most common is a hollow conductive metal pipe used to carry high frequency radio waves, particularly microwaves.

Figure 6:
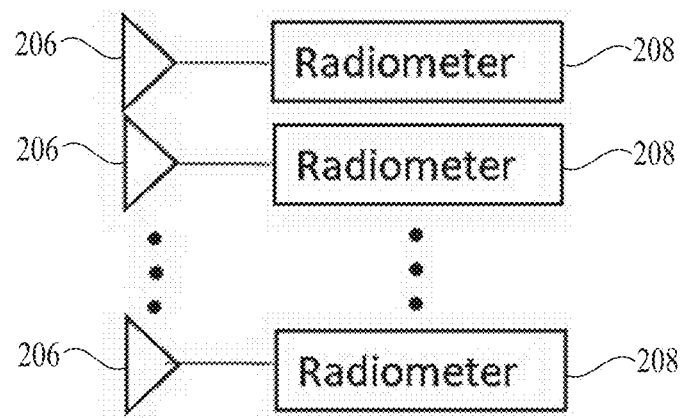
FIG. 6 is a block diagram of a Multiple Antenna Multiple Radiometer Type 1 microwave scanner configuration of the present invention.
Figure 7:
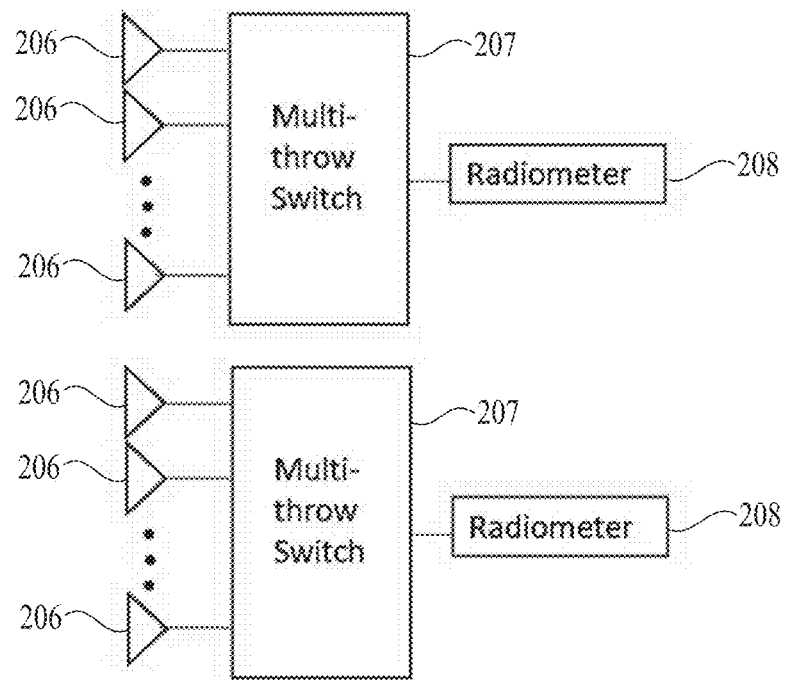
FIG. 7 is a block diagram of a dual Multiple Antenna Single Radiometer Type 2 configuration of the present invention.

As noted above, the microwave scanner 204 can comprise at least two different configurations. The Type 2 scanner 204 can comprise multiple antenna modules 206 with a single-channel radiometer 208 and a single multi throw microwave switch network 207 that selects which antenna module 206 is being used. This is shown in FIGS. 5, 6 and 7. FIG. 5 shows the block diagram of the microwave scanner 204 that is coupled to the garment 202 to form the type 2 hardware device 200. FIG. 6 shows type 1 configuration with several single-antenna 206-single-channel radiometer 208. The Type 3 configuration comprises at least one microwave switching network 207 coupling the multiple antenna module 206 and multiple channel radiometers 208. FIG. 7 shows a block diagram of a dual multiple antenna single channel radiometer configuration. Measurement samples from each antenna module 206 are collected in sequence. A microwave switch network 207 connects each antenna 205 (within each antenna module 206 via the microwave switch 210) to a radiometer 208 in sequence. The procedure to complete one cycle of measurements requires several minutes because the radiometer 208 is collecting measurements at each antenna 205 site, each of which requiring several seconds of integrated response. A microwave temperature reference and a reference temperature sensor 212 are provided at each antenna module 206 location. The radiometer 208 is effectively a Dicke type radiometer where every measurement is made with respect to the temperature reference supplied by the temperature sensor 212 located at each antenna module 206.

The Type 1 microwave scanner 204 (which, as noted above, is a subset of type 2 or type 3 M-S configurations) can comprise multiple dedicated radiometers 208, one for each antenna module 206. This configuration is shown in FIG. 6. An applicable version of the second configuration (dual type 2) is shown in FIG. 7, where the device 200 comprises two microwave scanners 204, one for each breast, and each microwave scanner 204 comprises multiple antenna modules 206 and one radiometer 208 for each breast. In this configuration, the total measurement time is reduced because both breasts can be scanned at the same time.

The microwave switch 210 connects each antenna 205 with its respective radiometer 208 in sequence via the microwave switch network 207. Optionally, the microwave switch 210 can comprise a multi-throw microwave switch. A multi-throw microwave switch essentially consists of combination of SPST (single-pole single throw) switches connected to a common junction and biased so that each switch port of the switch 210 can be enabled individually. The common junction of the switch 210 must be designed to minimize the resistive and reactive loading presented by the OFF ports in order to obtain low insertion loss and VSWR (voltage standing wave ratio) for the ON port. There are two basic methods of realizing a multi-throw microwave switch common junction for optimum performance over a broad frequency range. The first employs series mounted PIN diodes connected to the common junction. A path is selected by forward biasing its series diode and simultaneously reverse biasing all the other diodes. This provides the desired low-loss path for the ON port with a minimum of loading from the OFF ports. The second method utilizes shunt mounted PIN diodes located a quarter wavelength from the junction. The diode(s) of the selected ON port is reverse biased while the OFF ports are forward biased to create a short circuit across the transmission line. As a result of the quarter wavelength spacing, the short circuits are transformed to open circuits at the junction. By proper choice of transmission line impedances and minimization of stray reactance it is possible to construct a switch of this type with low insertion loss and VSWR over a three to one bandwidth. VSWR is defined for the input and output ports of the selected ON path. Similar switch configurations using FET devices instead of PIN diodes are often used for microwave switches like these.

Preferably, at least one temperature sensor 212 is located at each antenna module 206 site such that the number of antennas 205 the device 200 has will be equal to the number of temperature sensors 212 the system has. However, while this ratio for temperature sensors 212 to antennas 205 is not absolutely necessary, it is preferred for optimal detection of warmer tissue areas. The temperature sensors 212 provide a reference temperature reading of the surrounding environment (via the microwave termination connected to the switch 210) for comparison with the temperature reading obtained by accompanying antenna 205 to determine the temperature of the tissue within the field of view of the antenna. The difference between the reading of the temperature sensor 212 and the reading of the accompanying antenna 205, gives the temperature of the tissue within a volume of tissue under the antenna when added to the reference temperature reading.

The at least one controller 216 is located within the electronics module 214 and is configured to command the microwave switch network 207 switching sequence for radiometer 208 and the sequence of the temperature sensor 212 measurements and to collect both the radiometer 208 microwave measurements as well as the temperature sensor 212 measurements. The controller 216 is electrically coupled to each microwave scanner 204. Optionally the device 200 can have more than one controller 216.

The at least one data transmission device 218 is also located within the electronics module 214 and is electrically coupled to each scanner 204. Data transmission (also data communication or digital communications) is the transfer of data (a digital bit stream or a digitized analog signal) over a point-to-point or point-to-multipoint communication channel. Examples of such channels are copper wires, optical fibers, wireless (including microwave, optical and laser) communication channels, storage media and computer buses. As noted above, the data transmission device 218 transmits the measurement data collected by the controller 216 from the radiometers 208 and the temperature sensors 212 either to an electronic device 302, or directly to the data cloud storage 304. The measurement data can be wirelessly transmitted as an electromagnetic signal, such as an electrical voltage, radio wave, microwave, or infrared signal.

Optionally, the wireless communication technology can comprise Wi-Fi Direct, which was initially called Wi-Fi P2P (Peer to Peer). Wi-Fi Direct is a Wi-Fi standard that enables devices to easily connect with each other without requiring a wireless access point. Wi-Fi Direct allows two devices to establish a direct Wi-Fi connection without requiring a wireless router. Hence, Wi-Fi Direct is a single radio hop communication, not a multi-hop wireless communication, unlike wireless ad hoc networks and mobile ad hoc networks. Wi-Fi ad hoc mode, however, supports multi-hop radio communications, with intermediate Wi-Fi nodes as packet relays.

One advantage of Wi-Fi Direct is the ability to connect devices even if they are from different manufacturers. Only one of the Wi-Fi devices needs to be compliant with Wi-Fi Direct to establish a peer-to-peer connection that transfers data directly between them with greatly reduced setup.

Wi-Fi Direct negotiates the link with a Wi-Fi Protected Setup system that assigns each device a limited wireless access point. The "pairing" of Wi-Fi Direct devices can be set up to require the proximity of a near field communication, a UHF radio wave signal, or a button press on one or all the devices.

Once the measurement data arrives at the electronic device 302, the device 302 uploads the data to the cloud data storage 304. A service provider collects and processes the data from the cloud storage 304. Several algorithms and software, respectively, generate the thermogram images, perform image classifications, analyze the data and make the determination of suspicious sites, provide suitable feedback and analyze the results for the user and healthcare practitioner (physician) through the cloud distribution. Machine Deep Learning models and algorithms are applied to accommodate the growing body of data to enhance the thermal image classification algorithm accuracy.

Optionally, as noted above, the data can be transmitted directly to the cloud data storage 304 from the device 200. In this embodiment, the health practitioner can then access the uploaded data (and optionally processed data) via an electronic device 302 that is communicatively coupled (usually via wireless transmission means although it could be via wired means as well) to the cloud data storage 304.

The power source 220 can either be a power cord for coupling the garment 202 (and its scanners 204) to an electrical socket, or the power source module 220 can be a rechargeable battery coupled to battery charging and indicating circuitry or located within the electrical module 214. Optionally, the battery is rechargeable, either by wired or wirelessly recharging means, such as charging pads, charging bowls, or uncoupled radio frequency.

Charging pads typically use tightly-coupled electromagnetic inductive or non-radiative charging. Charging bowls or through-surface type chargers typically use loosely-coupled or radiative electromagnetic resonant charging that can transmit a charge a few centimeters. Uncoupled radio frequency (RF) wireless charging allows a trickle charging capability at distances of many feet.

Both tightly coupled inductive and loosely-coupled resonant charging operate on the same principle of physics: a time-varying magnetic field induces a current in a closed loop of wire.

Optionally, clip charging could be used where a clip is clipped onto the electronics module 214 to charge it (rather than the traditional wired method).

Optionally, the garment 202 can have both wired and wireless charging abilities.

The garment 202 has several advantages. First, it ensures stable and firm contact of the antennas 205 with the breast over the several minutes required to complete the measurement process. Second, it ensures accurate antenna 205 placement at the specified sites during subsequent measurements enabling temperature history comparisons for the purpose of long term monitoring and tracking. Third, the garment 202 provides for a comfortable measurement procedure for the users (both healthy and sick patients) and a much less tedious procedure for the instrument operator as compared to a single antenna/multiple antenna placement device. Fourth, the measurement could be self-administered, meaning the users could administer the testing in the privacy of their own home, rather than having to visit a clinic for testing. And fifth, it provides better microwave and thermal interference shielding against the external environment during the measurement process.

The use and function of all of the components will now be described in detail. As noted above, the microwave scanner 204 uses microwave radiometry to sense temperatures beneath the skin. The objective is to detect elevated temperatures of breast tissue resulting from increasing metabolic activity and the angiogenesis process that induces a temperature increase around a cancer cell region. The microwave scanner 204 compares the temperatures from multiple measurement sites to identify a suspicious warm spot in the area. Thermography using other "heat" sensing techniques, such as infrared, has been proposed for this purpose in the past. However, the advantage of a microwave scanner 204 of the present invention as compared to previously proposed approaches is that the microwave scanner 204 can measure the subsurface (subcutaneous) tissue temperatures which cannot be measured using other sensing devices. The availability of subcutaneous tissue temperature, which is a pathological and physiological biomarker, enables the potential early detection of cancer and its subsequent diagnosis.

Figure 8:
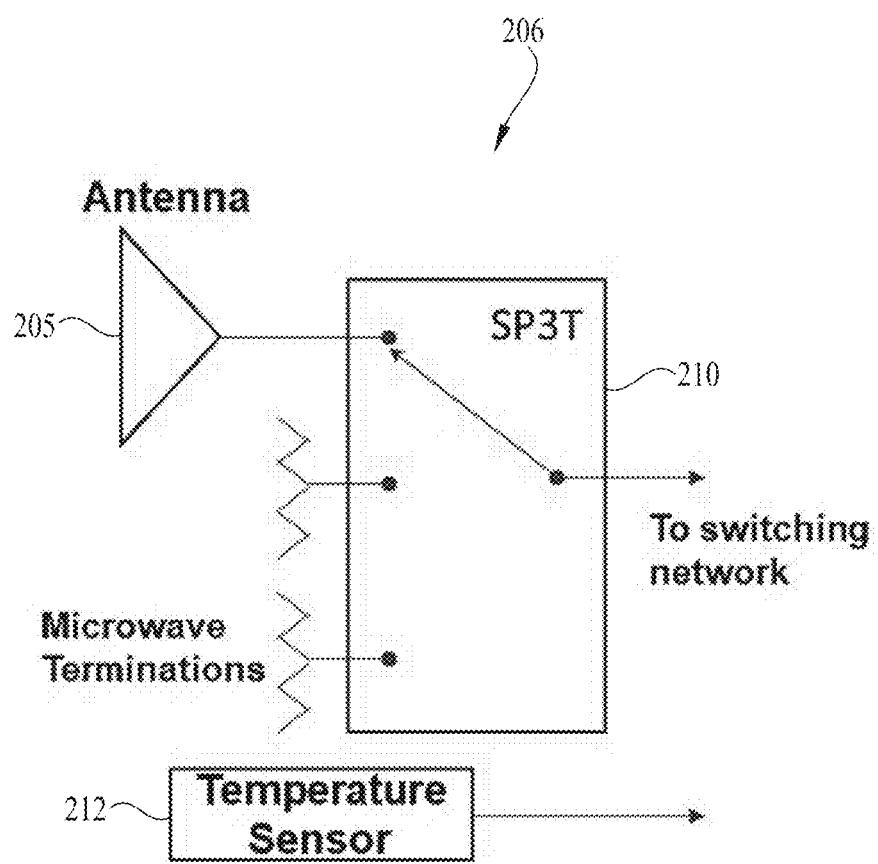
FIG. 8 is block diagram view of an antenna module of the present invention.

As noted above, the microwave scanner 204 can comprise multiple antennas 205 and multiple-channel radiometer 208 with antennas in contact with the skin to measure subcutaneous (subsurface) temperatures at multiple sites on the body. The antennas 205/antenna modules 206 are arrayed in a specific holder, such as the cup 201 coupled with bra-shaped garment 202 shown in FIGS. 1 and 2. As discussed above, FIG. 8 shows a block diagram of one antenna module 206. The antenna module 206 uses a single pole triple throw (SP3T) switch 210 to connect between the antenna 205 and two reference termination resistors. In normal temperature measurement mode, the switch 210 toggles between the antenna 205 and one of the reference termination resistors to produce the temperature difference reading between the breast tissue and the reference termination temperature sensor 212. In calibration mode, which is discussed in greater detail below, the switch 210 toggles between the two termination resistors, both of which are at the indicated temperature sensor. Being at the same temperature, the difference measurement should be zero. Any measured temperature other than zero is an error in the measurement path which will also be present in the normal measurement mode. The calibration temperature difference is read and then subtracted from the tissue temperature measurement to make the correction.

As noted above, the device 200 of the present invention uses microwave thermography to map temperature in tissue (breasts in this instance) in order to locate possible cancer tumor sites. In order for the device 200 to determine tissue temperature accurately, it is necessary to calibrate the microwave path between each antenna 205 and radiometer(s) 208. These paths can include lengths of coaxial cable and multi-throw microwave switches. The path to each antenna 205 from radiometer 208 will have different characteristics. The device 200 measures the temperature difference between the breast tissue within the antenna 205 field of view (FOV) and a reference termination resistor of known temperature located adjacent to the antenna 205. A microwave switch 210 in the antenna module 206 toggles between the antenna 205 and the reference termination resistor to make the temperature difference measurement. This temperature difference is added to the known reference termination temperature to provide the absolute temperature of the tissue under each antenna 205. In practice, conductor (coaxial cable) losses and small irregularities in the microwave path will produce measurement errors. These irregularities can cause offset error where the measured temperature is offset from the true tissue temperature by an unknown but fixed amount. The error can also be in the form of a gain error where the measured temperature is related to the magnitude of the temperature difference. The device 200 is configured with a method of determining and removing these measurement errors just prior to breast temperature measurement such that a correction for this type of measurement error can be made at each antenna module 206 site under the exact conditions of the measurement.

Figure 9:
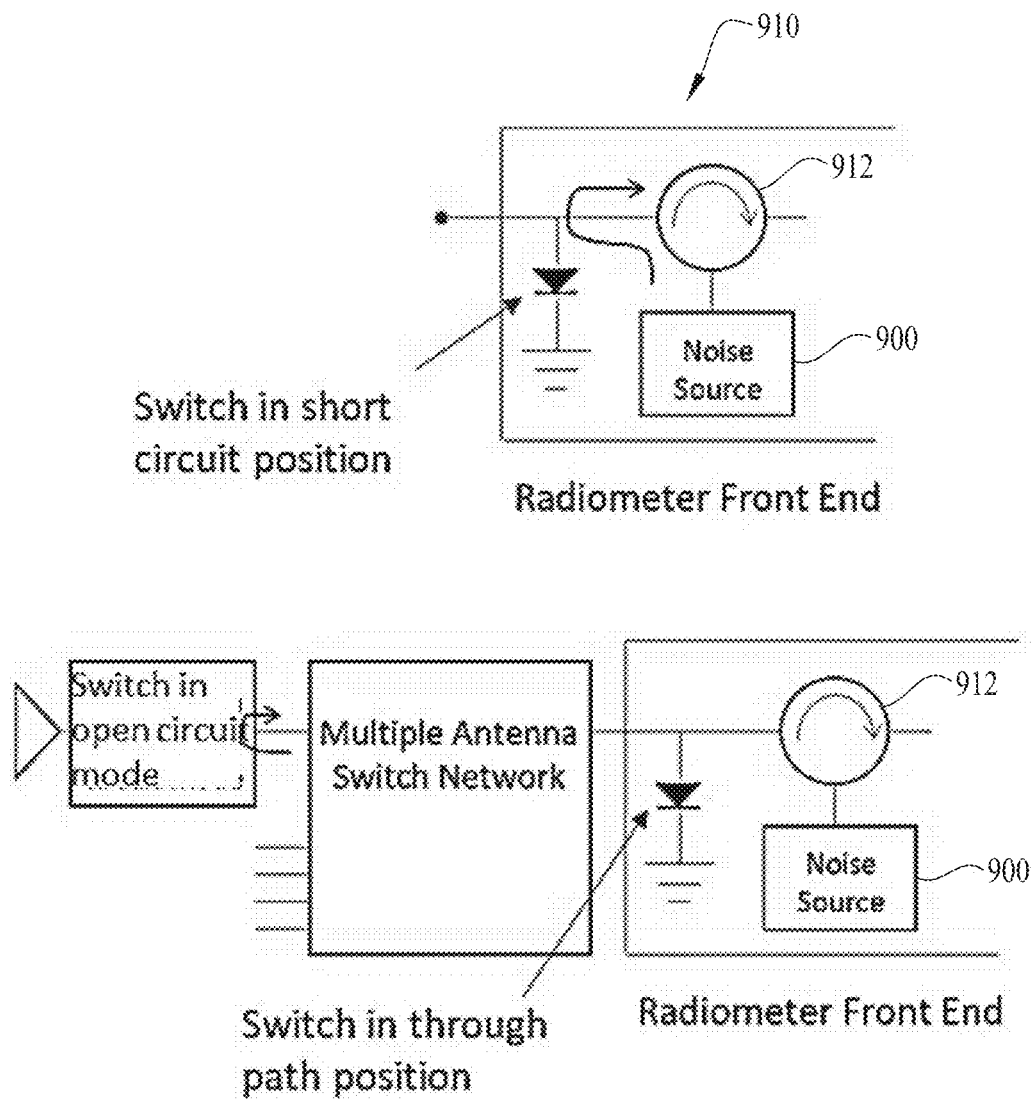
FIG. 9 is a schematic of a radiometer front end of the present invention.

The gain error is determined using the schematic shown in FIG. 9. A microwave noise source 900 is coupled onto the radiometer 208 at the radiometer input 910. FIG. 9 shows this coupling through a microwave circulator 912 but a directional coupler can also be used. Noise power propagates out through the radiometer input 910 connector toward the antenna module 206. This noise power is modulated in synchronization with the radiometer 208 detector clock. The antenna switch 210 is set to an open circuit position. The open circuit position exists when none of the three input legs is selected. Alternately, a four throw switch could be used and a short or open circuit attached to the selected fourth leg. The radiometer 208 measures the magnitude of the noise power reflected by the switch 210 in the open position and compares this value to the noise power measured when a switch internal to the radiometer 208 is set to a short circuit position. The ratio of the reflected power measured from the antenna switch 210 and the reflected power measured from the internal switch is twice the path loss between the radiometer 208 and the antenna module 206. The magnitude of the temperature measurement is then corrected for this path loss.

Figure 10:
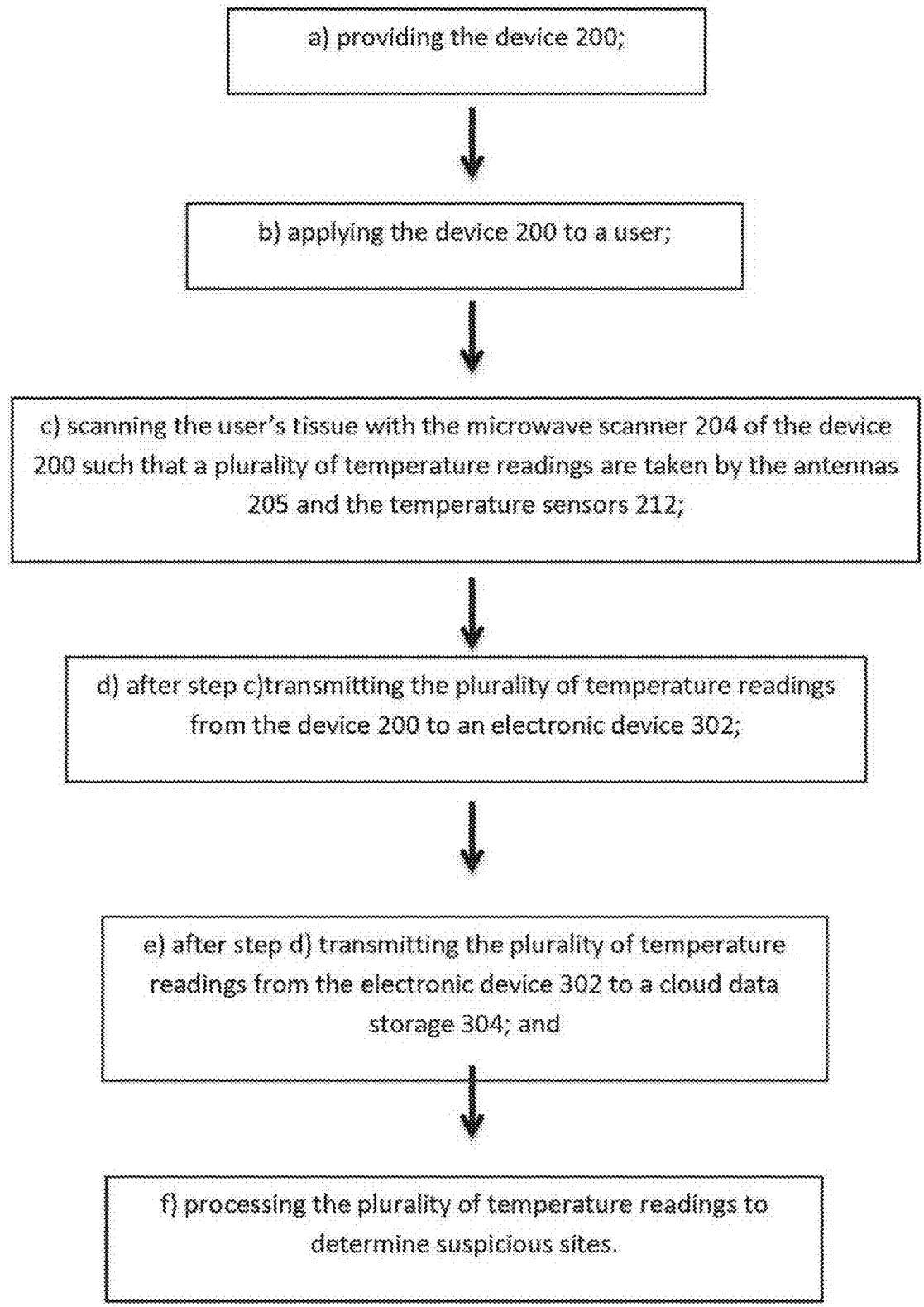
FIG. 10 is a view of flow chart of a method of detecting disease according to the present invention.

Also as noted above, in one aspect, the present invention comprises a method of detecting disease. The method is shown in FIG. 10 and comprises the steps of:

a) providing the device 200;
b) applying the device 200 to a user;
c) either manually or automatically, scanning the user's tissue with the microwave scanner 204 of the device 200 such that a plurality of temperature readings are taken by the antennas 205 and the temperature sensors 212;
d) after completing one cycle of measurements which takes place in step c), transmitting the plurality of temperature readings from the device 200 to an electronic device 302;
e) after step d) transmitting the plurality of temperature readings from the electronic device 302 to a cloud data storage 304; and
f) processing the plurality of temperature readings to determine suspicious sites.

Optionally, the processing in step f) can comprise generating at least one thermogram image and analyzing the processed data to determine and to classify suspicious areas.

Optionally, the device 200 can be applied by the users to themselves in the privacy of their own home. Then a physician can access the processed data via the cloud data storage 304 and provide guidance regarding same. This guidance can comprise a disease diagnosis which can be provided to the user via the internet to complete the process of tele-healthcare cycle.

Optionally, the method of detecting disease comprises the steps of:

a) receiving on an electronic device 302 from the device 200 a plurality of temperature readings taken by a plurality of antennas 206 and a plurality of temperature sensors 212;
b) transmitting the plurality of temperature readings from the electronic device 302 to a cloud data storage 304; and
c) processing the plurality of temperature readings to determine suspicious sites.

Figure 11:
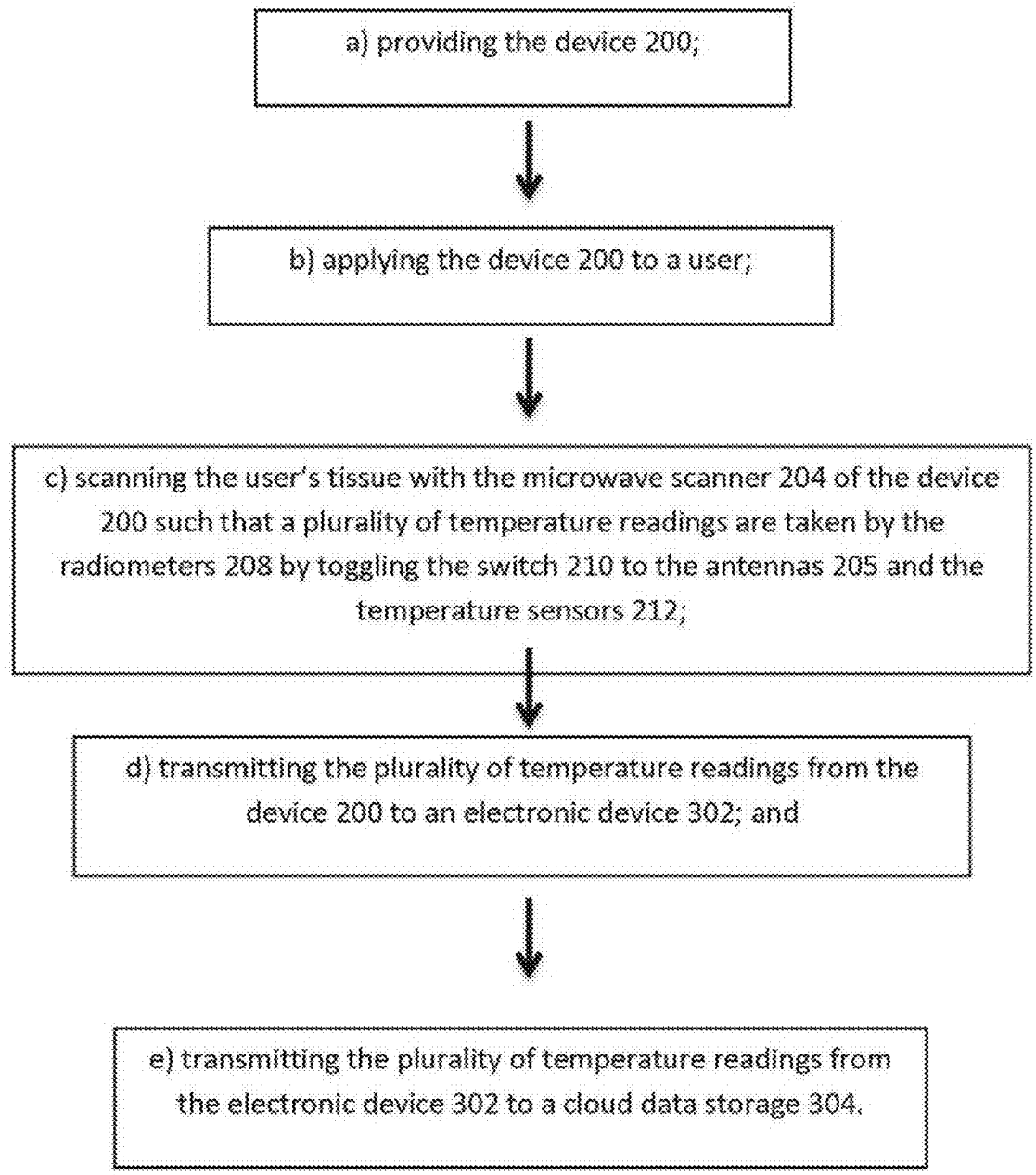
FIG. 11 is a view of flow chart of a method of using the device of FIG. 2.

Optionally, the present invention comprises a method of using the device 200 of the present invention. The method is shown in FIG. 11 and comprises the steps of:

a) providing the device 200;
b) applying the device 200 to a user;
c) scanning the user's tissue with the microwave scanner 204 of the device 200 such that a plurality of temperature readings are taken by the radiometer 208 by toggling the switch 210 to the antennas 205 and the temperature sensors 212;
d) transmitting the plurality of temperature readings to an electronic device 302;
e) transmitting the plurality of temperature readings from the electronic device 302 to a cloud data storage 304.

Optionally, the method of using the device 200 further comprises step f) processing the plurality of temperature readings to determine suspicious areas.

Optionally, the device 200 can be applied by the patient to themselves in the privacy of their own home. A physician can access the processed data via the cloud data storage 304 and provide guidance regarding same.

An additional method of using the device 200 of the present invention comprises the steps of:

a) receiving on an electronic device 304 from a device 200 a plurality of temperature readings taken by a plurality of antennas 206 and a plurality of temperature sensors 212;
b) transmitting the plurality of temperature readings from the electronic device 302 is 58 to 74 to a cloud data storage 304; and
c) processing the plurality of temperature readings to determine suspicious sites.

Figure 12:
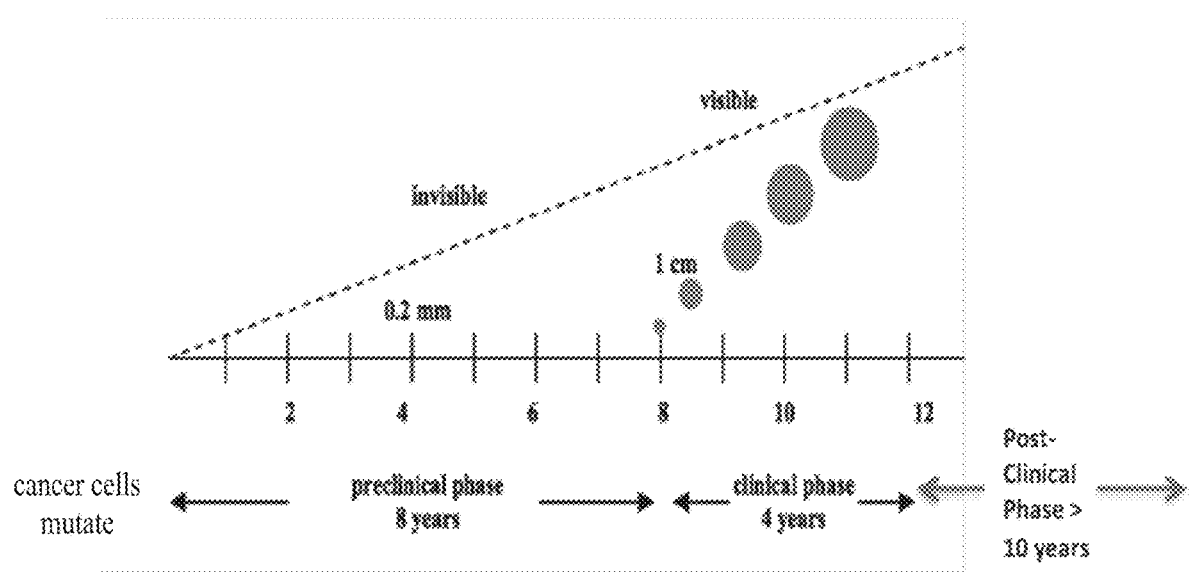
FIG. 12 is a diagram depicting the breast cancer life cycle, starting with cell mutation.

The breast cancer life cycle is depicted in FIG. 12. It consists of three phases: Phase (1) Pre-clinic phase—0 to 8 years after cancer cell mutations. Phase (2) Clinic phase—8 to 12 years after mutations; and Phase (3), Post-clinic phase—12 years after mutations. As an example of the various applications of the system 100 and device 200 of the present invention, it should be noted that the application and use of the system 100 and device 200 is different during the different phases of the cancer life cycle:

(1) During the pre-clinical phase, the user group is focusing on the women (and men) who are at the most risk for breast cancer. The primary objective is to continuously monitor and track the internal thermal profile variations to detect any thermal abnormalities caused by cancer, inflammation or other sickness.

(2) During the clinic phase, the user group includes medical professionals, such as physicians, nurses and other medical staff, as well as patients.

The device 200 can be used for breast cancer screening for women who have dense breast tissue and/or have microcalcifications to supplement/compliment the deficiencies of both mammography (X-ray) devices (which have low sensitivity for dense breast tissue) and ultra-sonography (ultrasound) devices (that cannot distinguish between microcalcification tissue from tumor cysts). In addition, the device 200 provides the thermal (temperature) data and information to assist physicians (and/or breast surgeons) to monitor the effectiveness and efficacy of their services, such as treatments of cancers. The device 200 provides thermal (temperature) data that can also assist the pathologist to more accurately differentiate the malignant tumor from benign tumor.

(3) During the post-clinical phase, the device 200 can provide early warning of cancer recurrence and metastases based on the continuous monitoring of thermal (temperature) abnormalities in the tissue of former cancer patients.

As noted above, one aspect of the present invention is implemented as a program, application, or product for use with a computer system and the device 200 of the present invention. The program(s) of the program product defines functions of the embodiments (including the methods and techniques described herein) and can be contained on a variety of computer-readable storage media. Illustrative computer-readable storage media include, but are not limited to: (i) non-writable storage media (e.g., read-only memory devices within a computer such as CD-ROM disks readable by a CD-ROM drive) on which information is permanently stored; and (ii) writable storage media (e.g., floppy disks within a diskette drive or hard-disk drive) on which alterable information is stored. Such computer-readable storage media, when carrying computer-readable instructions that direct the functions of the present invention, are embodiments of the present invention. Other media include communications media through which information is conveyed to a computer, such as through a computer or telephone network, including wireless communications networks. The latter embodiment specifically includes transmitting information to/from the Internet and other networks. Such communications media, when carrying computer-readable instructions that direct the functions of the present invention, are embodiments of the present invention. Broadly, computer-readable storage media and communications media may be referred to herein as computer-readable media.

The required APPs for IoMT connectivity are performing four basic functions to integrate the three segments into the system 100 as follows:

1) Hand shaking and data streaming between the mobile device with either Android or iOS and other mobile device platforms and microwave scanner:

2) Two-way data linking between mobile device and cloud server (or other type of big data base storage).

3) Raw data downloading and processed data, including graphics and images, uploading between cloud server storage and data analysis and processing station.

4) Processed data downloading and medical assessments and diagnosis message uploading between medical centers/hospital and cloud server.

Advantages of the Present Invention

The system 100 of the present invention can provide telemedicine and virtual clinic healthcare services for breast wellness and illness screening, include but not limited to, cancer prognosis and diagnosis. The screening can be done without any invasive procedures. The patient simply puts the garment 202 and scanner cups 201 on, the microwave scanner 204 is activated, and a plurality of temperature readings are taken. If any abnormal "hot spots" are noted in the tissue, the supervising physician now has an idea of exactly where to focus and perform any additional diagnostic techniques.

For sick persons and cancer patients—Due to the wireless data transmission capabilities of the system 100 and the portable nature of the device 200, the patient can administer the testing in the privacy of their own home or place, such as a hotel room, rather than having to visit a clinic or hospital. This saves the patient both time and money.

For physicians—the system 100 can increase the clinical efficiency by shortening clinic time as well as providing additional, valuable information from the processed image/data results of each patient's virtual visit. The system 100 can also extend the physician's patients geographical distributions.

For hospitals & clinic centers—the system 100 can reduce the patient visit frequency and hence decrease administrative load (cost saving for hospitals). The system 100 can also provide a better healthcare environment attributed to lessened traffic flow in hospital facilities.

Other applications of the present invention:

With the unique configuration of the microwave scanner 204, it can sense and measure the subcutaneous internal heat power density in terms of so-called radiometric temperature. Availability of subcutaneous radiometric temperature opens up a wide variety of medical applications that include, but are not limited to:

(1) detection of internal organ cancerous cells and abnormal tissues, such as cancers of the breast, lung, liver, pancreas, and ovary;

(2) identification of internal infection and/or inflammatory regions, such as arthritis, thyroid disease, and diagnosis of maxillary sinusitis;

(3) assistance with birth control;

4) providing thermogram images and temperature information to assist in the therapeutic treatment of disease, such as chiropractic thermal treatment, active microwave thermotherapy and ablation cancer therapy that require precise temperature control, as well as enhancement of the efficacy of acupuncture treatment; and (5) the radiometric temperature can be used to differentiate the malignant cancer cells from the benign cancer cells, and the thermal data can be used to increase biopsy accuracy and help to determine whether the biopsy is even necessary in the first place.

Although the present invention has been described in considerable detail with reference to certain preferred embodiments, other embodiments are possible. The steps disclosed for the present methods, for example, are not intended to be limiting nor are they intended to indicate that each step is necessarily essential to the method, but instead are exemplary steps only. Therefore, the scope of the appended claims should not be limited to the description of preferred embodiments contained in this disclosure. All references cited herein are incorporated by reference in their entirety.

What is claimed is:

1. A system for detecting disease, the system comprising:
 a) a device for detecting angiogenesis, the device comprising:
  i) two microwave scanners, each microwave scanner comprising:
   1) a cup:
   2) a flexible printed circuit board coupled to the cup, each circuit board comprising:
    a) a plurality of antenna modules coupled thereto, each antenna module comprising:
     i. an antenna configured to receive microwaves from patient tissue;
     ii. at least one multi-throw microwave switch coupled to the antenna; and iii. at least one temperature sensor located in close proximity to each antenna configured to take temperature measurements;
ii) at least one multiple channel radiometer coupled to the plurality of antenna modules by at least one coaxial cable, the radiometer configured to convert the measured microwaves emitted from patient tissue into measurement data;
iii) at least one microwave switch network coupled to the multi-throw microwave switch configured to perform a switching sequence;
iv) at least one controller electrically coupled to both microwave scanners and configured to:
 1) command both the microwave switch switching sequence and the sequence of the temperature sensor measurements; and
 2) collect measurement data from the radiometer and the temperature sensors used for detecting angiogenesis;
v) at least one data transmission device electrically coupled to the controller and configured to wirelessly transmit the measurement data collected by the controller from the radiometer and the temperature sensors to an electronic device; and
vi) at least one power source comprising at least one rechargeable battery; and
b) an electronic device comprising a smart phone, tablet, or computer, the electronic device configured to receive the measurement data from the data transmission device and transmit the measurement data to and receive processed data from a cloud data storage.

2. The system of claim 1, further comprising a cloud data storage configured to the measurement data from the electronic device.

3. A device for detecting angiogenesis, the device comprising:
a) two microwave scanners, each microwave scanner comprising:
 i) a flexible printed circuit board comprising:
  1) a plurality of antenna modules coupled thereto, each antenna module comprising:
   a) an antenna configured to receive microwaves from patient tissue;
   b) at least one multi-throw microwave switch coupled to the antenna; and
   c) at least one temperature sensor located in close proximity to each antenna configured to take temperature measurements;
 ii) at least one multiple channel radiometer coupled to the plurality of antenna modules by at least one coaxial cable, the radiometer configured to convert the measured microwaves emitted from patient tissue into measurement data;
 iii) at least one microwave switching network coupled to the multi-throw microwave switch and the radiometer configured to perform a switching sequence; and
b) at least one controller electrically coupled to both microwave scanners and configured to:
 i) command both the microwave switch switching sequence and the sequence of the temperature sensor measurements; and
 ii) collect measurement data from the radiometer and the temperature sensors used for detecting angiogenesis;
c) at least one data transmission device electrically coupled to the controller and configured to wirelessly transmit the measurement data collected by the controller from the radiometer and the temperature sensors to an electronic device; and
d) at least one power source comprising at least one rechargeable battery.

4. The device of claim 3, wherein the microwave scanner further comprises at least one cup and the at least one flexible printed circuit board is coupled to the at least one cup.

5. The device of claim 3, wherein the device is a garment with two cups and the microwave scanners are coupled to the cups.

6. The device of claim 5, wherein the garment cups comprises at least one piece of electrically conductive cloth.

7. The device of claim 5, wherein the garment is in the form of a bra.

8. A device for detecting angiogenesis, the device comprising:
a) at least one microwave scanner, the microwave scanner comprising:
 i) a flexible printed circuit board comprising:
  1) a plurality of antenna modules coupled thereto, each antenna module comprising:
   a) an antenna configured to receive microwaves from patient tissue;
   b) at least one multi-throw microwave switch coupled to the antenna; and
   c) at least one temperature sensor located in close proximity to each antenna configured to take temperature measurements;
b) at least one controller electrically coupled to the at least one microwave scanner and configured to:
 i) command both the microwave switch switching sequence and the sequence of the temperature sensor measurements; and
 ii) collect measurement data from the radiometer and the temperature sensors used to detect angiogenesis;
c) at least one data transmission device electrically coupled to the controller and configured to wirelessly transmit the measurement data collected by the controller from the radiometer and the temperature sensors to an electronic device; and
d) at least one power source.

9. The device of claim 8, wherein the microwave scanner further comprises at least one cup and the at least one flexible printed circuit board is coupled to the at least one cup.

10. The device of claim 8, wherein the device is a garment with two cups and each flexible printed circuit board is coupled to a cup.

11. The device of claim 9, wherein the cups comprises at east one piece of electrically conductive cloth.

12. The device of claim 10, wherein the garment is in the form of a bra.

13. The device of claim 8, wherein the power source comprises one of the following: a power cord or at least one rechargeable battery.

14. A method of using the device of claim 3, the method comprising the steps of:
a) providing the device;
b) placing the device on a user's skin;
c) scanning a user's subcutaneous tissue to produce measurement data from the radiometers and temperature sensors;
d) transmitting the measurement data from the device to an electronic device; and e) transmitting the measurement data from the electronic device to a cloud data storage.

15. The method of claim 14, further comprising step f) after step e), processing the measurement data to determine suspicious sites in the user's tissue.

16. A method of using the device of claim 3, the method comprising the steps of:
   a) providing the device;
   b) placing the device on a user's skin;
   c) scanning a user's subcutaneous tissue to produce measurement data from the radiometers and temperature sensors; and
   d) transmitting the measurement data from the device to a cloud data storage.

17. The method of claim 16, further comprising step e) after step d), processing the measurement data to determine suspicious sites in the user's tissue.

* * * * *